US006649607B2

(12) United States Patent
Leventer et al.

(10) Patent No.: US 6,649,607 B2
(45) Date of Patent: Nov. 18, 2003

(54) COMPOSITIONS AND METHODS FOR TREATING OR PREVENTING CONVULSIONS OR SEIZURES

(75) Inventors: Steven M. Leventer, Langhorne, PA (US); Robert Kucharik, Glenmoore, PA (US)

(73) Assignee: Vela Pharmaceuticals, Inc., Lawrenceville, NJ (US)

( * ) Notice: Subject to any disclaimer, the term of this patent is extended or adjusted under 35 U.S.C. 154(b) by 1 day.

(21) Appl. No.: 10/008,516

(22) Filed: Nov. 8, 2001

(65) Prior Publication Data
US 2003/0055048 A1 Mar. 20, 2003

Related U.S. Application Data
(60) Provisional application No. 60/292,026, filed on May 18, 2001.

(51) Int. Cl.[7] .................. A61K 31/5513; A61K 31/33; C07C 209/00
(52) U.S. Cl. .................. 514/221; 514/183; 514/218; 514/219; 564/302
(58) Field of Search .................. 564/302; 514/219, 514/218, 183, 221

(56) References Cited

U.S. PATENT DOCUMENTS

| 3,736,315 | A | 5/1973 | Kőrösi et al. ............... 260/239 |
| 4,322,346 | A | 3/1982 | Kőrösi et al. ............... 260/239 |
| 4,423,044 | A | 12/1983 | Kőrösi et al. ............... 424/244 |
| 4,614,740 | A | 9/1986 | Láng et al. .................. 514/221 |
| 4,835,152 | A | 5/1989 | Kőrösi et al. ............... 514/221 |
| 5,204,343 | A | 4/1993 | Andrási et al. .............. 514/221 |
| 5,459,137 | A | 10/1995 | Andrási et al. .............. 514/220 |
| 5,519,019 | A | 5/1996 | Andrási et al. .............. 514/220 |
| 5,521,174 | A | 5/1996 | Andrási et al. .............. 514/220 |
| 5,639,751 | A | 6/1997 | Andrási et al. .............. 514/220 |
| 5,795,886 | A | 8/1998 | Anderson et al. ............ 514/220 |
| 5,891,871 | A | 4/1999 | Xia et al. .................... 514/219 |
| 6,017,965 | A | 1/2000 | Mueller et al. .............. 514/649 |
| 6,051,610 | A | 4/2000 | Mueller et al. .............. 514/628 |
| 6,071,970 | A | 6/2000 | Mueller et al. .............. 514/648 |
| 6,075,018 | A | 6/2000 | Vágó et al. .................. 514/221 |
| 6,080,736 | A | 6/2000 | Landry et al. ............... 514/221 |

FOREIGN PATENT DOCUMENTS

| CA | 2057504 | 6/1992 |
| DE | DT 2122 070 | 6/1972 |
| EP | 0 492 485 | 7/1992 |
| HU | 178516 | 9/1981 |
| WO | WO 91/17159 | 11/1991 |
| WO | WO 92/11262 | 7/1992 |
| WO | WO 95/01357 | 1/1995 |
| WO | WO 00/24400 | 5/2000 |

OTHER PUBLICATIONS

S. Almquist et al., "Direct and Indirect Approaches to Enantiomeric Separation of Benzodiazepines Using Micro Column Techniques," *J. Chromatography A*, 679:139–146 (1994).

(List continued on next page.)

Primary Examiner—Frederick Krass
Assistant Examiner—Clinton Ostrup
(74) Attorney, Agent, or Firm—Fish & Neave; James F. Haley, Jr.; R. Minako Pazdera

(57) ABSTRACT

The present invention relates to compositions comprising S-tofisopam substantially free of R-tofisopam, and methods for treating or preventing convulsions and/or seizures comprising administration of the composition to subjects in need of treatment therefor. Also provided are compositions and methods for treating or preventing convulsions and/or seizures comprising administering S-tofisopam substantially free of R-tofisopam with another anti-convulsant.

22 Claims, 6 Drawing Sheets

OTHER PUBLICATIONS

N. Bargmann–Leyder et al., "A Comparison of LC and SFC for Cellulose–and Amylose–Derived Chrial Stationary Phases," *Chirality*, 7:311–325 (1995).

A. Bond and M. Lader, "A Comparison of the Psychotropic Profiles of Tofisopam and Diazepam," *Eur. J. Clin. Pharmacol.*, 22:137–142 (1982).

M. Briley et al., "Tofisopam Enhances the Anticonvulsant Activity of Diazepam Against Some, but Not All, Convulsive Agents," *Bristish J. Pharm.*, 82:300P (1984).

G. De Sarro et al., "GYKI 52466 and Related 2,3–benzodiazepines as Anticonvulsant Agents in DBA/2 Mice," *Eur. J. Pharmacol.*, 294:411–422 (1995).

I. Fellegvári et al., "Separation of Conformational Diastereomers of 2,3–Benzodiazepines by HPLC," Chromatography in Symposia Biologica Hungarica, H. Kalász and L.S. Ettre, Eds., 193–203 (1987).

V. Filip et al., "A Double–Blind, Placebo–Controlled Study with Tofizopam in Anxiety Neurosis," *Agressologie*, 22:27–30 (1981).

I. Fitos et al., "Separation of Enantiomers of Benzodiazepines on the Chiral–AGP Column," *J. Chromatography A*, 709:265–273 (1995).

E. Fogassy et al., "Studies on the Properties and Structure of Optically Active 1–(3, 4–Dimethoxyphenyl)–4–Methyl–5–Ethyl–7, 8–Dimethoxy–5H–2,3–Benzodiazepine (Tofizopam)," in *Bio–Organic Heterocycles*, H.C. van der Plas, L. Ötvös, and M. Simonyi, Eds., 229–233 (1984).

H. Goldberg et al., "Comparative Efficacy of Tofisopam and Placebo," *Am. J. Psychiatry*, 136:196–199 (1979).

K. Imre et al., "A Tofizopam (Grandaxin®) Farmakokinetikaja es Metabolizmusa," *Acta Pharmaceutica Hungarica*, 63:83–90 (1993).

C. Ito, "Behavioral Pharmacological Study on the Structure Activity Relationship of Benzodiazepine Derivatives: with Particular Reference to the Activity of 2,3–Benzodiazapine," *J. Tokyo Med. College*, 39:369–384 (1981).

J. Kanto et al., "Tofizopam: a Benzodiazepine Derivative without Sedative Effect," *Intl. J. Clin. Pharm. Ther. Tox.*, 20:309–312 (1982).

K. Maier et al., "The Effect of Tofisopam on Psychic Performance in Persons With More Than Average Anxiety: A Controlled Experimental Trial," *Current Therapeutic Research*, 35(4):541–548 (1984).

"Tofisopam", Martindale, Royal Pharmaceutical Society of Great Britain, p. 620, col. 1 (1993).

T. Mennini et al., "Brain Levels of Tofisopam in the Rat and Relationship with Benzodiazepine Receptors," *Arch. Pharmacol.*, 321:112–115 (1982).

J. Molcan et al., "Tofizopam in the Therapy of Anxious–Depressive Syndroms," *Agressologie*, 22:23–24 (1981).

F. Pal, "A Grandaxin® Gyógyszertechnológiája," *Acta Pharmaceutica Hungarica*, 63:67–78 (1993).

Pakkanen et al., "Comparative Study of the Clinical Effects of Tofizopam, Nitrazepam and Placebo as Oral Premedication," *British J. Anaesthesia*, 1009–1012 (1980).

S. Pellow and S. File, "The Effects of Tofisopam, a 3,4–Benzodiazepine, in Animal Models of Anxiety, Sedation, and Convulsions," *Drug Dev. Res.*, 7:61–73 (1986).

L. Petócz and I. Kosóczky, "The Main Pharmacological Characteristics of Grandaxin (Tofisopam, EGYT–341)," *Ther. Hungarica*, 23:134–138 (1975).

L. Petócz, "The Pharmacological Effects of Tofisopam (Grandaxin)®," *Acta Pharmaceutica Hungarica*, 63:79–82 (1993).

V. Saano and A. Urtti, "Tofizopam Modulates the Affinity of Benzodiazepine Receptors in the Rat Brain," *Pharm. Biochem. Behavoir*, 17:367–369 (1982).

V. Saano, "Tofisopam Selectively Increases the Action of Anticonvulsants," *Med. Biol.*, 64:201–206 (1986).

V. Saano et al., "Tofisopam Enhances the Action of Diazepam Against Tremor and Convulsions," *Med. Biol.*, 61:49–53 (1983).

T. Seppälä et al., "Tofisopam, a Novel 3,4–Benzodiazepine: Multiple–Dose Effects on Psychomotor Skills and Memory. Comparison with Diazepam and Interactions with Ethanol," *Psychopharmacology*, 69:209–218 (1980).

M. Simonyi and I. Fitos, "Stereoselective Binding of a 2,3–Benzodiazepine to Human Serum Albumin," *Biochemical Pharmacology*, 32(12):1917–1920 (1993).

R. Sladká et al., "A Placebo–controlled Clinical Trial With Tofizopam in the Treatment of Anxiety Neurosis," *Ther. Hungarica*, 27:176–180 (1979).

J. Szegó et al., "Selected Passages From the Clinical–Pharmacological and Clinical Trials of Grandaxin®," Acta Pharmaceutica Hungarica, 63:91–98 (1993).

G. Toth et al., "Racemate Splitting of (±)–5–ethyl–1–(3, 4–dimethoxyphenyl)–6,7–dimethoxy–4–methyl–5H–2, 3–benzodiazepine an Anomalous Chiroptic Behavior of Enantiomer (1)," *J. Heterocyclic Chem.*, 20:709–713 (1983).

G. Várady et al., "The Clinical Evaluation of Grandaxin Used in the Treatment of Outpatients (A Multicentric Study)," *Ther. Hungarica*, 23:153–158 (1975).

J. Visy and M. Simonyi, "The Role of Configuration and Conformation in the Binding of 2,3–Benzodiazepines to Human Serum Albumin," *Chirality*, 1:271–275 (1989).

F. Zsila et al., "Separation and Identification of Tofisopam and Steroisomers by Hyphenated HPLC–CD Technique," *J. Liq. Chrom. & Rel. Technol.*, 22:713–719 (1999).

COMPOSITIONS AND METHODS FOR TREATING OR PREVENTING CONVULSIONS OR SEIZURES

This application claims benefit from U.S. Provisional Application No. 60/292,026 filed May 18, 2001.

FIELD OF THE INVENTION

The present invention relates to compositions and methods for treating or preventing convulsions or seizures.

BACKGROUND OF THE INVENTION

Tofisopam is 1-(3,4-dimethoxy-phenyl)-4-methyl-5-ethyl-7,8-dimethoxy-5H-2,3-benzodiazepine, which can be represented by the formula:

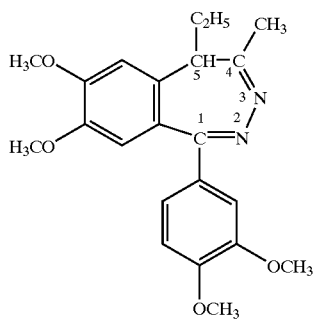

Tofisopam (racemic mixture) has been marketed under the names Grandaxin® and Seriel® as an anxiolytic. Although tofisopam is a benzodiazepine, it differs structurally from the classical diazepam-like benzodiazepines in that the nitrogen atoms in the ring structure are positioned at 2,3 instead of 1,4. Despite the structural similarity between tofisopam and classical 1,4-benzodiazepines, the difference in position of the nitrogen in the benzodiazepine ring confers pharmacological activity on tofisopam that is very different from classical benzodiazepines.

A synthesis of tofisopam is described in U.S. Pat. No. 3,736,315. Tofisopam has a chiral center at carbon C-5 and therefore has two enantiomers. In addition, each enantiomer of tofisopam can exist in two stable conformations based on the two configurations that can be assumed by the nitrogen containing benzodiazepine ring.

The molecular structure and conformational properties of tofisopam have been determined by NMR, CD and x-ray crystallographic methods (Visy, J. and Simongi, M., *Chirality* 1:271–275 (1989)). The 2,3 diazepine ring exists in two kinds of boat conformation. In the major conformers, (+)R and (−)S, the ethyl group attached to the center of asymmetry C-5 has a quasiequatorial orientation, while in the minor conformers, (−)R and (+)S, the ethyl group is positioned quasiaxially. Thus, racemic tofisopam can exist as four molecular species, i.e., two enantiomers each of which exists in two chiral conformations. The sign of optical rotation is reversed upon inversion of the diazepine ring. In crystal form, tofisopam exists only as the major conformations, with levorotatory tofisopam being of the (S) absolute configuration (Toth, G. et al.,*J. Heterocyclic Chem.* 20:709–713 (1983); Fogassy, E. et al., In: *Bio-Organic Heterocycles*, Van der Plas, H. C., Ötvös, L., Simongi, M., eds. Budapest Amsterdam: Akademia; Kiado-Elsevier, 229:233 (1984)).

The absolute configuration of an asymmetric drug molecule can have profound effects on the efficacy of the drug. Fogassy et al., states that an abstract by Petocz et al. from a 1980 meeting describes pharmacological tests in mice which show different biological activity for the stereoisomers of tofisopam, including the observation that the activity of racemic tofisopam does not correspond with the sum of the activities of its enantiomers (Fogassy, E. et al., supra). However, Fogassy et al. does not describe the biological assays of the specific results achieved by Petocz et al. Furthermore, a search of the prior art yielded no such abstract by Petocz et al. Thus, there is currently no indication that Petocz et al. exists or relates to S-tofisopam and its unexpected properties.

In addition the binding of tofisopam enantiomers to human serum albumin has been reported to be stereoselective and affected by the interconversion of conformations (Simonyi, M., and Fitos, I., *Biochem Pharmacology* 32:1917–1920 (1983)).

Hungarian Patent No. 178516 describes an attempt to separate the enantiomers of tofisopam and observations relating to the administration of the separated products in mice. However, the purity of the separated products administered to the mice is not reported. Further, the absolute configuration of the separated products is not reported, and none of the tests in mice measured the anti-convulsant activity of the separated products.

There have been two reports that tofisopam exhibits anti-convulsant activity in mice. In 1981, C. Ito alleged that tofisopam can inhibit convulsions induced by tryptamine in mice (Ito, C., *Tokyo Med. College* 39:369–384 (1981); hereinafter "Ito"). However, the convulsion data of Ito does not support this conclusion. The administration of tofisopam according to the tests described in Ito appeared to have no effect on decreasing the incidence of convulsions in the mice (Table 6, Ito supra). Furthermore, Ito did not test the anti-convulsant activity of S-tofisopam substantially free of R-tofisopam.

In 1986, Pellow et al. reported that the administration of 100 mg/kg of tofisopam reduced the number of mice having convulsions induced by the compound Ro 5-4864 (Pellow, S. and File, S., *Drug Dev. Res.* 7:61–73 (1986)). However, Pellow et al. also reported that all of the treated mice still experienced myoclonic jerks. In contrast, Pellow et al. reported that 25–50 mg/kg tofisopam had proconvulsant activity in Tuck No. 1 mice when administered in combination with 3 mg/kg picrotoxin or 30 mg/kg pentylenetetrazole. Pellow et al. also reported that a dose of 10–50 mg/kg of tofisopam had no affect on the number or severity of convulsions in Tuck No. 1 mice that had been given 6 mg/kg of picrotoxin. Likewise, in Tuck No. 1 mice that were given 60 mg/kg of pentylenetetrazole, a dose of 10–25 mg/kg of tofisopam was reported to have no effect as an anti-convulsant. Pellow et al. did not test the anti-convulsant activity of S-tofisopam substantially free of R-tofisopam.

Numerous other reports, some of which were published after 1986, state that tofisopam has no anti-convulsant properties (Mennini et al., *Arch. Pharmacol.* 32:112–115 (1982); Saano, V., *Med. Bio.* 64:201–206 (1986); Petocz, L., *Acta Pharm. Hung.* 63:79–82 (1993); Szego, J. et al., *Acta Pharm. Hung.* 63:91–98 (1993)). None of the studies tested the anti-convulsant activity of S-tofisopam substantially free of its (R) enantiomer.

Tofisopam has been reported to enhance the actions of benzodiazepine anti-convulsants but not phenytoin, sodium valproate or carbamazepine (Saano, V., *Med. Biol.* 64:201–206 (1986)). For example, the potentiation action of tofisopam was reported to be effective with diazepam against convulsions (Briley, M. *Br. J. Pharmacol.* 82:300P (1984); Mennini, T., *Naugn-Schmiedeberg's Arch Pharmacol.* 321:112–115 (1982)), and against tremors (Saano, V., *Pharmacol Biochem. Behav.* 17:367–369 (1982); Saano, V., *Med. Biol.* 61:49–53 (1983)). None of these potentiation studies examined the effects of either of the enantiomers of tofisopam on the anti-convulsant activity of diazepam or other anti-convulsants.

SUMMARY OF THE INVENTION

An object of this invention is to provide new compositions and methods for treating and preventing convulsions and seizures. The present invention provides a composition comprising a therapeutically effective amount of S-tofisopam substantially free of its (R) enantiomer, and a pharmaceutically acceptable carrier. A composition comprising a prodrug or pharmaceutically acceptable salt of S-tofisopam substantially free of R-tofisopam is also contemplated.

Preferably, the amount of S-tofisopam or pharmaceutically acceptable salt thereof is 80% or more by weight of the total weight of tofisopam. More preferably, the amount of S-tofisopam or pharmaceutically acceptable salt thereof is 85% or more by weight of the total weight of tofisopam. More preferably, the amount of S-tofisopam or pharmaceutically acceptable salt thereof is 90% or more by weight of the total weight of tofisopam. More preferably, the amount of S-tofisopam or pharmaceutically acceptable salt thereof is 95% or more by weight of the total weight of tofisopam. Most preferably, the amount of S-tofisopam or pharmaceutically acceptable salt thereof is 99% or more by weight of the total weight of tofisopam. In one aspect of the invention, the conformation of the S-tofisopam is 80% (−) and 20% (+).

The present invention also provides compositions comprising S-tofisopam substantially free of its (R) enantiomer, and one or more other anti-convulsants. According to one embodiment, the other anti-convulsant is selected from the group consisting of phenytoin, mephenytoin, ethotoin, phenobarbital, mephobarbital, primidone, carbamazepine, ethosuximide, methsuximide, phensuximide, valproic acid, trimethadione, paramethadione, phenacemide, acetazolamide, progabide, diazepam, lorazepam, clonazepam, clorazepate and nitrazepam. In one embodiment, the other anti-convulsant is a benzodiazepine. In one preferred embodiment, the other anti-convulsant is a 1,4-benzodiazepine. In yet another preferred embodiment, the other anti-convulsant is diazepam, lorazepam, clonazepam, clorazepate or nitrazepam.

In one embodiment, the pharmaceutical composition is a controlled-release pharmaceutical composition.

The present invention provides methods of treating convulsions or seizures comprising administering to a subject in need of treatment therefor, a therapeutically effective amount of S-tofisopam substantially free of R-tofisopam sufficient to alleviate the convulsions or seizures. Another embodiment of the invention relates to methods of preventing convulsions or seizures in a subject at risk for developing convulsions or seizures comprising administering to the subject a therapeutically effective amount of S-tofisopam substantially free of its (R) enantiomer sufficient to prevent the convulsions or seizures. Administration of a prodrug or pharmaceutically acceptable salt of S-tofisopam according to the methods of this invention is also contemplated.

In another embodiment of this invention, the subject in need of treatment is suffering from convulsions or seizures caused by a disorder or condition selected from the group consisting of epilepsy, acquired immunodeficiency syndrome (AIDS), Parkinson's disease, Alzheimer's disease, other neurodegenerative disease including Huntington's chorea, schizophrenia, obsessive compulsive disorders, tinnitus, neuralgia, trigeminal neuralgia, amyotrophic lateral sclerosis (ALS), tics (e.g., Gille de la Tourette's syndrome), post-traumatic epilepsy, alcohol use, alcohol withdrawal, intoxication or withdrawal from barbiturates, brain illness or injury, brain tumor, choking, drug abuse, electric shock, fever (especially in young children), head injury, heart disease, heat illness, high blood pressure, meningitis, poisoning, stroke, toxemia of pregnancy, uremia related to kidney failure, venomous bites and stings, withdrawal from benzodiazepines, febrile convulsions, and afebrile infantile convulsions. In one preferred embodiment, the subject is suffering from convulsions or seizures caused by epilepsy.

The present invention also provides methods of treating of preventing convulsions or seizures comprising administering to a subject in need of treatment therefor a therapeutically effective amount of S-tofisopam, prodrug or salt thereof, substantially free of R-tofisopam together or sequentially with one or more other anti-convulsants. The other anti-convulsant can be selected from the group consisting of, but not limited to, phenytoin, mephenytoin, ethotoin, phenobarbital, mephobarbital, primidone, carbamazepine, ethosuximide, methsuximide, phensuximide, valproic acid, trimethadione, paramethadione, phenacemide, acetazolamide, progabide, diazepam, lorazepam, clonazepam, clorazepate and nitrazepam. In one embodiment, the other anti-convulsant is a benzodiazepine. In one preferred embodiment, the other anti-convulsant is a 1,4-benzodiazepine. In yet another preferred embodiment, the other anti-convulsant is diazepam, lorazepam, clonazepam, clorazepate or nitrazepam.

DETAILED DESCRIPTION OF THE INVENTION

Figure 1:
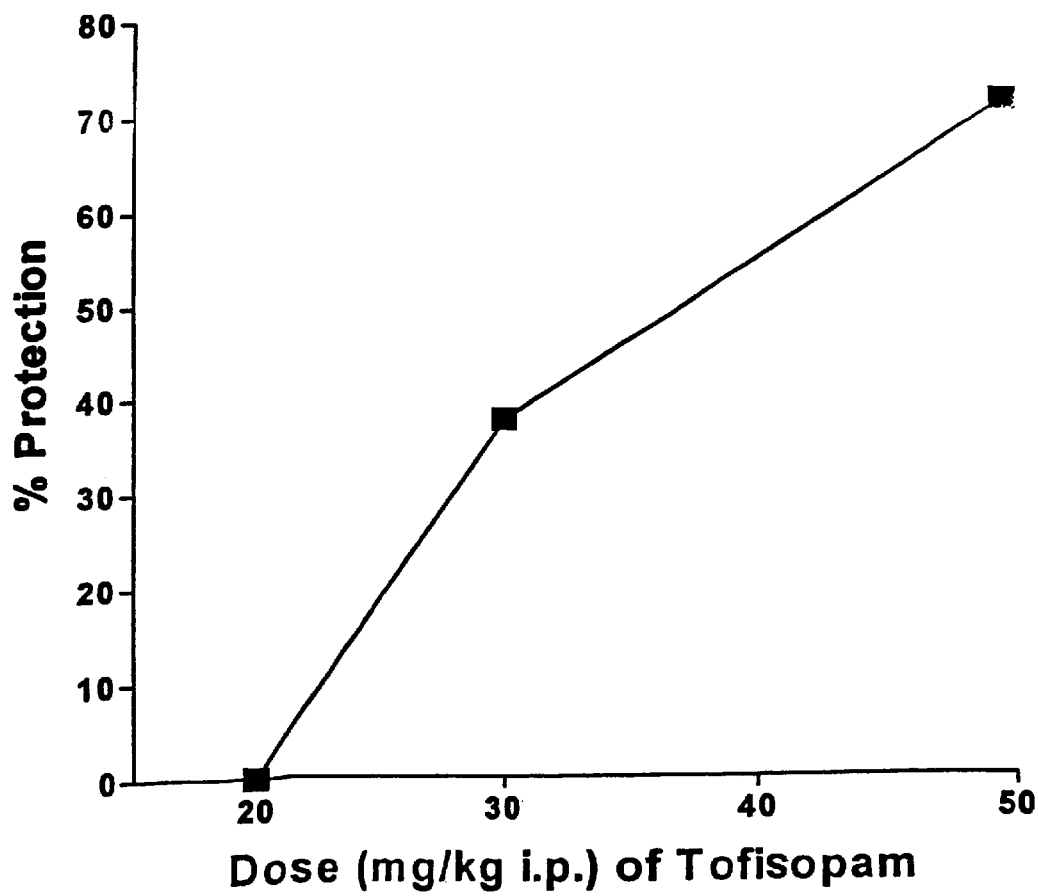
FIG. 1 graphically depicts the dose-dependent effect of tofisopam on picrotoxin-induced seizures in male NSA mice.

A composition according to this invention comprises S-tofisopam substantially free of its (R) enantiomer. The term "substantially free of its (R) enantiomer" as used herein means that the composition comprises at least 80% or more by weight of S-tofisopam and 20% by weight or less of R-tofisopam in terms of total weight of tofisopam. In a preferred embodiment, the composition comprises at least 85% or more by weight of S-tofisopam and 15% by weight or less of R-tofisopam in terms of total weight of tofisopam. In a more preferred embodiment, the composition comprises at least 90% or more by weight of S-tofisopam and 10% by weight or less of R-tofisopam in terms of total weight of tofisopam. In yet a more preferred embodiment, the composition comprises at least 95% or more by weight of S-tofisopam and 5% or less of R-tofisopam in terms of total weight of tofisopam. In a most preferred embodiment, the composition comprises at least 99% or more by weight of S-tofisopam and 1% or less of R-tofisopam in terms of total weight of tofisopam. In one embodiment, the confirmation of S-tofisopam is 80% (−) and 20% (+).

Tofisopam can be synthesized according to methods known in the art. For example, a method for synthesis is described in U.S. Pat. Nos. 3,736,315 and 4,423,044, the disclosures of which are incorporated by reference. The (S) enantiomer of tofisopam can be obtained by the methods described herein (Example 1 or 3).

The compositions of the present invention comprise S-tofisopam, substantially free of R-tofisopam, or a prodrug or a pharmaceutically acceptable salt thereof as the active ingredient, and can also contain a pharmaceutically acceptable carrier and optionally other therapeutic ingredients.

In one embodiment, the composition of the present invention comprises S-tofisopam and one or more other anti-convulsants. The other anti-convulsant can be, e.g., phenytoin, mephenytoin, ethotoin, phenobarbital, mephobarbital, primidone, carbamazepine, ethosuximide, methsuximide, phensuximide, valproic acid, trimethadione, paramethadione, phenacemide, acetazolamide, progabide, diazepam, lorazepam, clonazepam, clorazepate or nitrazepam. In another embodiment, the composition of this invention comprises S-tofisopam and a benzodiazepine. In yet another embodiment, the composition of this invention comprises S-tofisopam and a 1,4-benzodiazepine. In yet a further embodiment, the composition of this invention comprises S-tofisopam and an anti-convulsant selected from the group consisting of diazepam, lorazepam, clonazepam, clorazepate and nitrazepam.

Prodrugs according to this invention are inactive derivatives of S-tofisopam that are metabolized in vivo into the active agent in the body. Prodrugs useful according to this invention are those that have substantially the same or better therapeutic value than S-tofisopam in treating or preventing convulsions or seizures. For example, a prodrug useful according to this invention can improve the penetration of the drug across biological membranes leading to improved drug absorption; prolong duration of the action of the drug, e.g., slow release of the parent drug from the prodrug and/or decrease first-pass metabolism of the drug; target the drug action; improve aqueous solubility and stability of the drug (e.g., intravenous preparations, eyedrops etc.); improve topical drug delivery (e.g., dermal and ocular drug delivery); improve the chemical and/or enzymatic stability of drugs (e.g., peptides); or decrease side effects due to the drug. Methods for making prodrugs are know in the art (e.g., Balant, L. P., *Eur. J. Drug Metab. Pharmacokinet.* 15:143–153 (1990); and Bundgaard, H., *Drugs of the Future* 16:443–458 (1991); incorporated by reference herein).

The term "pharmaceutically acceptable salt" refers to salts prepared from pharmaceutically acceptable non-toxic acids including inorganic acids and organic acids. Since S-tofisopam is basic, salts can be prepared from pharmaceutically acceptable non-toxic acids including inorganic and organic acids. Such acids include malic, acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are hydrobromic, hydrochloric, maleic, phosphoric, and sulfuric acids.

The compositions according to this invention can be prepared for oral, rectal, or transdermal use, e.g., using a patch. Alternatively, compositions can be prepared for sublingual or parenteral administration (including subcutaneous, intramuscular, intrathecal and intravenous administration). The most suitable route in any given case will depend on the nature and severity of the condition being treated. According to one preferred aspect of this invention, the route of administration is the oral route. According to another preferred aspect of this invention, the route of administration is rectal, intramuscular, intranasal or intravenous. According to yet another preferred aspect of the invention, the route of administration is intraperitoneal or subcutaneous. The composition can be presented in a unit dosage form and prepared by any of the methods well-known in the art of pharmacy.

In practical use, S-tofisopam or prodrug or salt thereof, substantially free of R-tofisopam, can be combined as the active ingredient in admixture with a pharmaceutical carrier according to conventional pharmaceutical compounding techniques. The carrier can take a wide variety of forms depending on the form of preparation desired for administration, e.g., oral or parenteral administration (including intravenous injections or infusions). For example, carriers according to this invention include starches, sugars, microcrystalline cellulose, stabilizers, diluents, granulating agents, lubricants, binders, fillers and disintegrating agents. Compositions for oral dosage form can include any of the usual pharmaceutical media, e.g., water, glycols, oils, alcohols, flavoring agents, preservatives, coloring agents and the like in the case of oral liquid preparations, e.g., suspensions, elixirs and solutions; or aerosols.

The compositions of the present invention can also be formulated so as to provide slow or controlled-release of the active ingredient therein using, e.g., hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

For example, U.S. Pat. No. 5,674,533 discloses controlled-release compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a gangliosideliposome vehicle. U.S. Pat. No. 5,639,476 discloses a stable solid controlled-release formulation having a coating derived from an aqueous dispersion of a hydrophobic acrylic polymer. These patents are incorporated herein by reference.

Biodegradable microparticles can be used in the controlled-release formulations of this invention. For example, U.S. Pat. No. 5,354,566 discloses a controlled-release powder that contains the active ingredient. U.S. Pat. No. 5,733,566, describes the use of polymeric microparticles that release antiparasitic compositions. These patents are incorporated herein by reference.

The controlled-release of the active ingredient can be stimulated by various inducers, for example pH, temperature, enzymes, water, or other physiological conditions or compounds. Various mechanisms of drug release exist. For example, in one embodiment, the controlled-release component can swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient (e.g., S-tofisopam or salt thereof) in the pharmaceutical composition. In another embodiment, the controlled-release component is biodegradable, induced by exposure to the aqueous environment, pH, temperature, or enzymes in the body. In another embodiment, sol-gels can be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Pharmaceutical stabilizers can also be used to stabilize compositions containing S-tofisopam or prodrug or salts thereof; acceptable stabilizers include but are not limited to L-cysteine hydrochloride, glycine hydrochloride, malic acid, sodium metabisulfite, citric acid, tartaric acid and L-cysteine dihydrochloride.

Dosage forms according to the invention include tablets, coated tablets, caplets, capsules (e.g., hard gelatin capsules), troches, dragées, dispersions, suspensions, solutions, patches, pills, coated pills, and the like, including sustained release formulations well known in the art. See, e.g. *Introduction to Pharmaceutical Dosage Forms*, 1985, Ansel, H. C., Lea and Febiger, Philadelphia, Pa.; *Remington's Pharmaceutical Sciences*, 1995, Mack Publ. Co., Easton, Pa. For example, compositions of the present invention suitable for oral administration can be presented as discrete units such as soft gelatin capsules, cachets, tablets, pills, or aerosol sprays, each containing a predetermined amount of the active ingredient. Alternatively, compositions of the present invention can be in the form of a powder or granules or as a solution or a suspension in an aqueous liquid, a non-aqueous liquid, an oil-in-water emulsion, or a water-in-oil liquid emulsion. Such compositions can be prepared by any of the methods of pharmacy but all methods include the step of bringing into association the active ingredient with the carrier. A preferred solid oral preparation is tablets. A more preferred solid oral preparation is coated tablets. If desired, tablets can be coated by standard aqueous or nonaqueous techniques.

In general, the compositions can be prepared by uniformly and intimately admixing the active ingredient or prodrug with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with one or more of a binder, filler, stabilizer, lubricant, inert diluent, and/or surface active or dispersing agent. Molded tablets can be made by molding in a suitable machine a mixture of the powdered compound moistened with an inert liquid diluent.

In one embodiment, each tablet contains from approximately 10 mg to approximately 100 mg of the active ingredient or prodrug, and each cachet or capsule contains from approximately 10 mg to approximately 300 mg of the active ingredient or prodrug. In another embodiment, the tablet, cachet or capsule contains one of four dosages: approximately 10 mg, approximately 50 mg, approximately 100 mg, and approximately 150 mg of active ingredient or prodrug.

In the case where the composition comprises an anticonvulsant other than S-tofisopam, salt or prodrug thereof, the other anticonvulsant can be present in an amount less than, greater than, or equal to the amount of S-tofisopam, salt or prodrug thereof, as physically allowed by the pharmaceutical arts.

In a preferred embodiment, the subject to be treated according to the methods of the invention is a mammal. In another preferred embodiment, the subject to be treated according to the methods of this invention is a human.

Convulsions according to this invention are involuntary muscle contractions caused by abnormal neuronal activity resulting in contortion of the body and/or limbs. Seizures according to this invention are transient changes of behavior induced by the disordered, synchronous and rhythmic firing of neurons. Periodic unpredictable occurrences of seizures are commonly associated with epilepsy. The two main types of epileptic seizures are partial seizures and generalized seizures. Partial seizures as used herein, are characterized as those that affect neurons limited to part of one cerebral hemisphere. Partial seizures can or can not be accompanied by impairment of consciousness. Generalized seizures as used herein, include those in which both hemispheres are involved and consciousness is usually impaired. Generalized seizures include absence seizures, myoclonic seizures, clonic seizures, tonic seizures, tonic-clonic seizures and atonic seizures (Dreifuss et al., Classification of Epileptic Seizures and the Epilepsies and Drugs of Choice for Their Treatment, p. 1–9, In: Antiepileptic Drugs: Pharmacology and Therapeutics, Eds M. J. Eadie and F. J. E. Vajda; Wilder et al., Classification of Epileptic Seizures, p. 1–13, In: Seizure Disorders, A Pharmacological Approach to Treatment, Raven Press, New York (1981)).

Pseudoepileptic or non-epileptic seizures can be caused by a definable medical cause, e.g., cardiovascular disease including arrhythmias, aortic stenosis, and orthostatic hypotension; toxic or metabolic disorders including hypoglycemia and drug toxicity; or sleep disorders. Non-epileptic seizures can also be induced by psychiatric conditions, e.g., hysteria, schizophrenia.

Convulsions or seizures can result from disorders or specific conditions, e.g., epilepsy, acquired immunodeficiency syndrome (AIDS), Parkinson's disease, Alzheimer's disease, other neurodegenerative disease including Huntington's chorea, schizophrenia, obsessive compulsive disorders, tinnitus, neuralgia, trigeminal neuralgia, amyotrophic lateral sclerosis (ALS), tics (e.g., Gille de la Tourette's syndrome), post-traumatic epilepsy, alcohol use, alcohol withdrawal, intoxication or withdrawal from barbiturates, brain illness or injury, brain tumor, choking, drug abuse, electric shock, fever (especially in young children), head injury, heart disease, heat illness, high blood pressure, meningitis, poisoning, stroke, toxemia of pregnancy, uremia related to kidney failure, venomous bites and stings, withdrawal from benzodiazepines, febrile convulsions, and afebrile infantile convulsions.

The magnitude of a prophylactic or therapeutic dose of the active ingredient (e.g., S-tofisopam or salt thereof) or S-tofisopam prodrug and, if desired, other anticonvulsant for treating or preventing convulsions or seizures will vary with the severity of the patient's affliction and the route of administration. The dose and dose frequency will also vary according to the age, weight and response of the individual patient. In general, the recommended daily dose range for the conditions described herein can lie within the range of from approximately 10 mg to approximately 1200 mg per day, generally divided equally into doses given one to four times a day. A daily dose range can be between 50 mg and 600 mg per day, usually divided equally into a one to four times a day dosing. Alternatively, a daily dose range can be between 100 mg and 400 mg per day, usually divided equally into a two to four times a day dosing. It can be necessary to use dosages outside these ranges in some cases and adjust the amounts of S-tofisopam, salt or prodrug thereof administered alone or in combination with the other anti-convulsant(s). The treating physician will know how to increase, decrease or interrupt treatment based upon patient response. The various terms described above such as "therapeutically effective amount," are encompassed by the above-described dosage amounts and dose frequency schedule.

For use in treating or preventing convulsions or seizures, the physician will generally prescribe the period of treatment and frequency of dose of S-tofisopam, substantially free of R-tofisopam, on a patient-by-patient basis. In general, however, treatment or prevention of convulsions or seizures with S-tofisopam, prodrug or salt thereof substantially free of R-tofisopam, can be carried out for as long a period as necessary, either in a single, uninterrupted session or in discrete sessions. For example, therapy can be carried out for a period of 4 to 18 weeks.

According to the methods of this inventio, S-tofisopam, salt or prodrug thereof can be administered alone or in combination with one or more other anti-convulsants to treat or prevent convulsions or seizures including myoclonic jerks (i.e., clonic activity). The other anti-convulsant can be selected from the group consisting of, ut is not limited to, phenytoin, mephenytoin, ethotoin, phenobarbital, mephobarbital, primidone, carbamazepine, ethosuximide, methsuximide, phensuximide, valproic acid, trimethadione, paramethadione, phenacemide, acetazolamide, progabide, diazepam, lorazepam, clonazepam, clorazepate and nitrazepam. The other anti-convulsant can be included in the composition comprising S-tofisopam, salt or prodrug thereof. Alternatively, the other anti-convulsant can be administered simultaneously with the composition comprising S-tofisopam, salt or prodrug thereof, or at any time during the treatment of the subject with the composition. According to one aspect of the invention, S-tofisopam is administered together with at least one other benzodiazepine to treat or prevent convulsions or seizures. In another aspect of the invention, S-tofisopam is administered together with at least one other 1,4-benzodiazepine. In yet another aspect of the invention, S-tofisopam is administered together with diazepam, lorazepam, clonazepam, clorazepate or nitrazepam to treat or prevent convulsions or seizures.

Any suitable route of administration may be employed for providing the subject of this invention with an effective dosage of S-tofisopam substantially free of R-tofisopam. For example, oral, rectal, parenteral, transdermal, subcutaneous, sublingual, intranasal, intramuscular, intraperitoneal, intrathecal and the like can be employed as appropriate.

Throughout this specification, the word "comprise" or variations such as "comprises" or "comprising" will be understood to imply the inclusion of a stated integer or group of integers but not the exclusion of any other integer or group of integers.

U.S. Provisional Application No. 60/292,026 filed May 8, 2001, is hereby incorporated by reference herein in its entirety.

The present invention is illustrated in the following examples. However, it should be noted that these examples are for illustrative purposes only and are not to be construed as restricting the invention in any manner.

EXAMPLE 1

Resolution of S-Tofisopam

The enantiomers of tofisopam were resolved by chiral chromatography. For example, tofisopam (42.8 mg dissolved in acetonitrile) was loaded onto a Chirobiotic V column (ASTEC, Whippany, N.J.). Elution of the compounds with MTBE/ACN 90/10 (v/v), 40 ml/min, was monitored at 310 nm, 2 mm path. The R(+) enantiomer was the first compound to elute from the column. R(−) tofisopam ("A'"), S(−/+) tofisopam ("B" and "B'"), and residual R(+) tofisopam ("A") co-eluted and was collected in a subsequent fraction.

The S(−) enantiomer was isolated from fraction 2 by the following protocol. Fraction 2 was dried, re-dissolved in 1 ml of acetonitrile and loaded onto a Chirobiotic V column. Peak B and B' was shave recycled over a Chirobiotic V column two more times (MTBE/ACN 90/10 (v/v), 40 ml/min monitored at 310 nm, 2 mm path). A peak containing S(−) tofisopam was collected from the third recycle, dried and stored for use in biological assays.

The final preparations of R- and S-tofisopam were assayed for enantiomeric purity by two different groups. One group reported that the final preparation of R-tofisopam was 98% pure (i.e., enantiomeric excess of 96%), and that of S-tofisopam was 95% pure (i.e., enantiomeric excess of 90%). The second group reported that the R-tofisopam was greater than 97.5% pure (i.e., enantiomeric excess of >95%), and that the S-tofisopam was 87% pure (i.e., enantiomeric excess of 74%), as determined by analytical chromatography. Analytical evaluations of the starting material and final preparations of R- and S-tofisopam as performed by the second group was carried out using Chiral Tech OD GH060 columns (Daicel) (hexane/IPA 90/10, 25° C., detection at 310 nm). We believe that the results of the analysis of the purity of R- and S-tofisopam obtained by the second group were correct. The second group was also the group that tested the enantiomeric purity of the R-and S-tofisopam obtained as described in Example 3 below.

EXAMPLE 2

Evaluation of Tofisopam and its Enantiomers as Anti-Convulsants

Picrotoxin was used as the convulsing agent and diazepam, an established anti-convulsant, was used as a control. Anticonvulsant activity against picrotoxin-induced seizures is considered evidence of clinical antiepileptic potential and reason for further evaluation of a test compound's anticonvulsant profile (Swinyard, E. A. et al., General principles: experimental detection, quantification and evaluation of anticonvulsants. In: Antiepileptic Drugs, D. M. Woodbury et al., eds. Raven Press, New York (1990) pp. 111–126).

Male NSA mice weighing approximately 20–25 g, were injected intraperitonealy (i.p.) with various doses (8–10 animals/dose) of diazepam, tofisopam, R-tofisopam of Example 1, or S-tofisopam of Example 1, 15 minutes prior to picrotoxin injection. Picrotoxin (5 mg/kg, Sigma Chem. Co., St. Louis, Mo., USA) was dissolved in saline and administered subcutaneously to induce seizures. In addition, picrotoxin alone was administered to seven animals as a control. All test drugs were dissolved in dimethylsulfoxide (DMSO). Both S- and R-tofisopam displayed a yellow color when dissolved in DMSO.

After picrotoxin injection, mice were placed into a plexiglass cage for 30 minutes of observation. The appearance of seizures was defined as the presence of a single episode of clonic or tonic activity (including myoclonic jerks) during the 30 minute observation period. The drug vehicle DMSO did not have any effect on seizure activity at the concentration used. Animals were euthanized immediately after the observation period by $CO_2$ inhalation. The $ED_{50}$ (the dose of test compound at which half of the animals were protected against picrotoxin-induced seizures) values and their 95% confidence limits were calculated by the method of Litchfield and Wilcoxon (*J. Pharmacol. Exp. Ther.* 96:99–113 (1949)). Results of these experiments are summarized in Table 1 below.

The effect of tofisopam on picrotoxin-induced seizures in NSA mice is shown in FIG. 1. Racemic tofisopam produced a dose-dependent inhibition (expressed as percent protection) of picrotoxin-induced seizures in mice when administered by the intraperitoneal route. The $ED_{50}$ (95% confidence limits) value was 37.8 (28.2–50.8) mg/kg.

Figure 2:
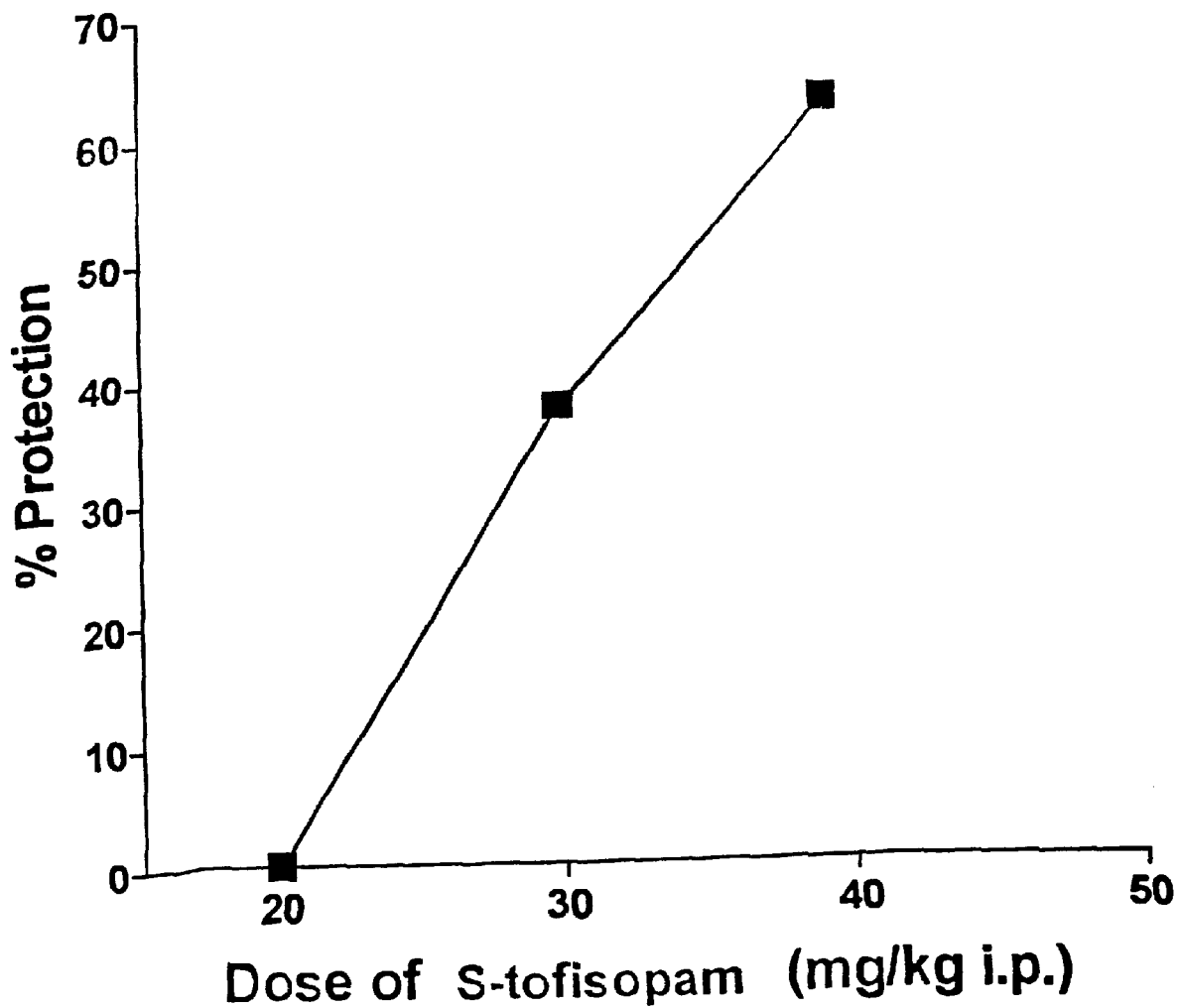
FIG. 2 graphically depicts the dose-dependent effect of S-tofisopam on picrotoxin-induced seizures in male NSA mice.

R-tofisopam did not inhibit picrotoxin-induced convulsions at either 20 or 50 mg/kg. On the other hand, the (S) enantiomer exhibited anti-convulsant activity with over 60% protection at 40 mg/kg. (see FIG. 2). An estimate of the $ED_{50}$ (95% confidence limits) of S-tofisopam was 35 (28–43) mg/kg.

TABLE 1

Summary of Anti-convulsant $ED_{50}$ Values for Compounds Tested

| Compound Tested | $ED_{50}$ (95% confidence limit) mg/kg |
| --- | --- |
| diazepam | 0.52 (0.24–1.08) |
| tofisopam | 37.8 (28.2–50.8) |
| R-tofisopam | Inactive |
| S-tofisopam | 35 (28–43) |

These data indicate that both racemic and S-tofisopam have intrinsic anti-convulsant activity against picrotoxin-induced seizures in NSA mice. In contrast, the (R) enantiomer of tofisopam showed no anti-convulsant activity.

EXAMPLE 3

Preparation of Tofisopam Enantiomers

Tofisopam diastereomer salts were prepared using the following procedure. (1) 3.0 g of racemic tofisopam was first dissolved in 10 ml of chloroform, after which 10 ml of distilled water was added to the dissolved racemate (solution A). (2) In a separate container, 1.5 g of D- or L-dibenzoyl-tartaric acid (DBTA) was dissolved in 20 ml chloroform (molar ratio of 0.56 of DBTA to tofisopam) (solution B). The mixture was stirred and heated to 45° C. until dissolution was complete. DB-(L)-TA (characterized by negative optical rotation) was used to purify R-tofisopam, whereas DB-(D)-TA (characterized by positive optical rotation) was used to purify S-tofisopam. (3) Solutions A and B were mixed and stirred until precipitation was complete. The mixture was then cooled to 5° C. to enhance yield. The solids were filtered, washed three times with 4 ml of cold chloroform, and dried.

To dissociate the tofisopam diastereomer salts and recover the resolved tofisopam, the dried material was (4) suspended in 50 ml of 0.5M NaOH and then stirred for 2 hours with 10 ml of chloroform. (5) The aqueous phase was separated away and discarded, and the chloroform layer was evaporated to dryness. (6) The solids were then triturated with 50 ml of 5% acetic acid until the gummy paste became granular. (7) The resulting solids were filtered and dried. (8) The pH of the filtrate was raised by at least 10 by using solid sodium hydroxide pellets and stirring for one hour. The solids were then filtered and dried. Production of S-tofisopam with an enantiomeric purity of 96% (i.e., enantiomeric excess of 92%) required four enrichment cycles of the resolution procedure, wherein the solids obtained at the end of the above procedure were redissolved and steps 1–8 were repeated.

The final preparation of R-tofisopam and S-tofisopam was 95.6% pure (i.e., enantiomeric excess of 91.2%) and 96% pure (i.e., enantiomeric excess of 92%), respectively, as determined by analytical chromatography.

EXAMPLE 4

Evaluation of Tofisopam and its Enantiomers as Anti-Convulsants

The preparations of the tofisopam enantiomers of Example 3, as well as racemic tofisopam and diazepam, were tested using the picrotoxin-induced convulsion assay as described in Example 2. Results of these experiments are summarized in Table 2 below.

Figure 3:
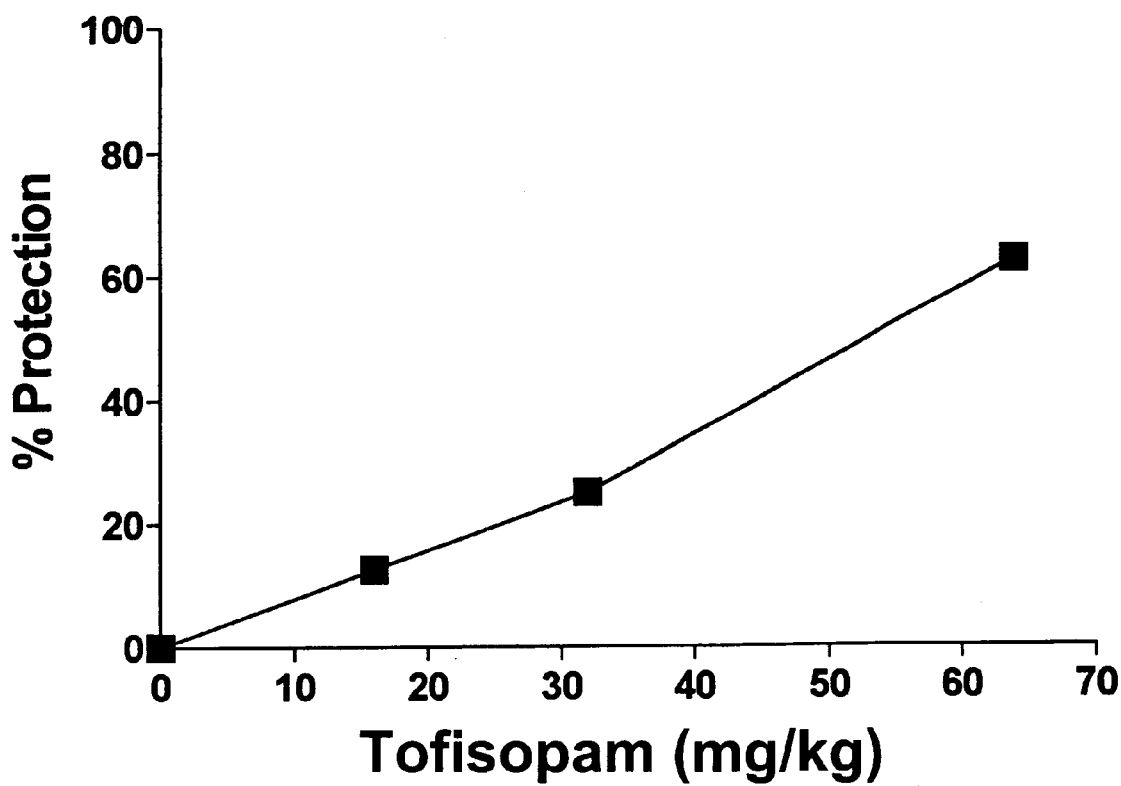
FIG. 3 graphically depicts the dose-dependent anti-convulsant effect of racemic tofisopam on picrotoxin-induced seizures in male NSA mice.
Figure 4:
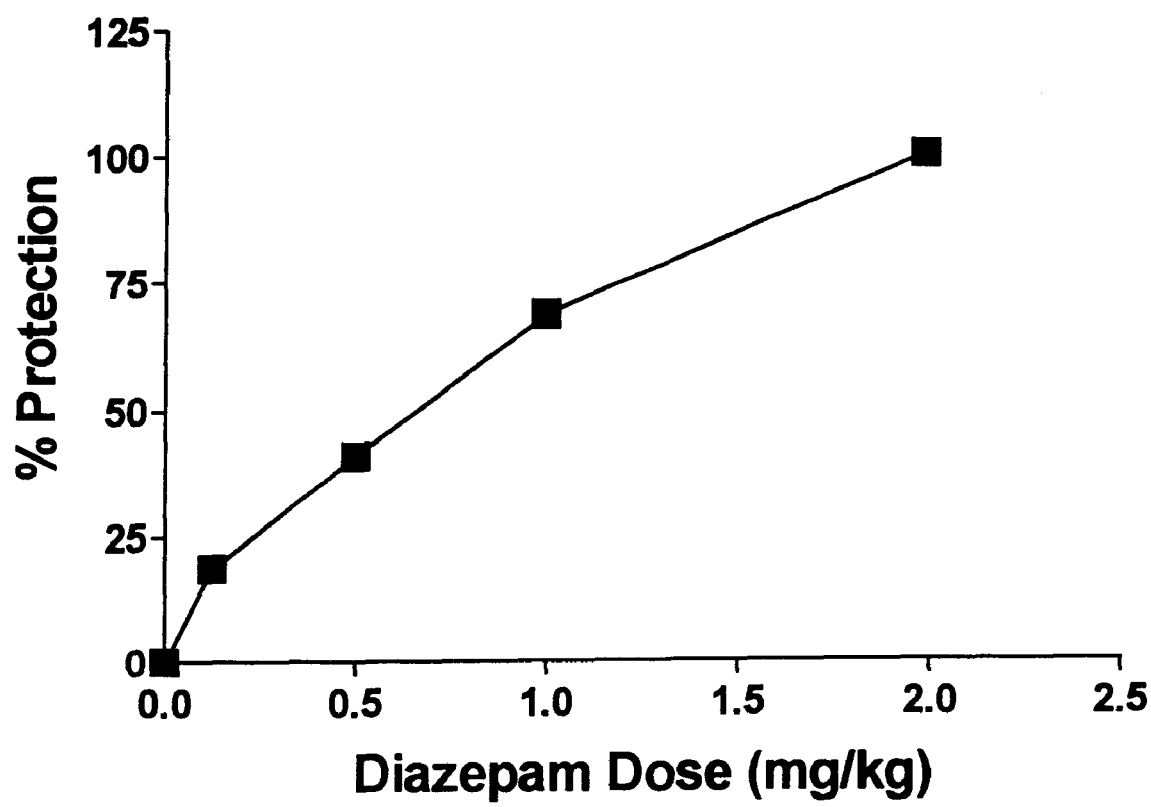
FIG. 4 graphically depicts the dose-dependent anti-convulsant effect of diazepam on picrotoxin-induced seizures in male NSA mice.

Racemic tofisopam produced a dose-dependent inhibition of picrotoxin-induced seizures in mice with an $ED_{50}$ (95% confidence limits) value of 51.4 (26.8–98.5) mg/kg (see FIG. 3). Diazepam also produced a dose-dependent anticonvulsant activity with an $ED_{50}$ (95% confidence limits) value of 0.45 (0.27–0.77) mg/kg (see FIG. 4).

Figure 5:
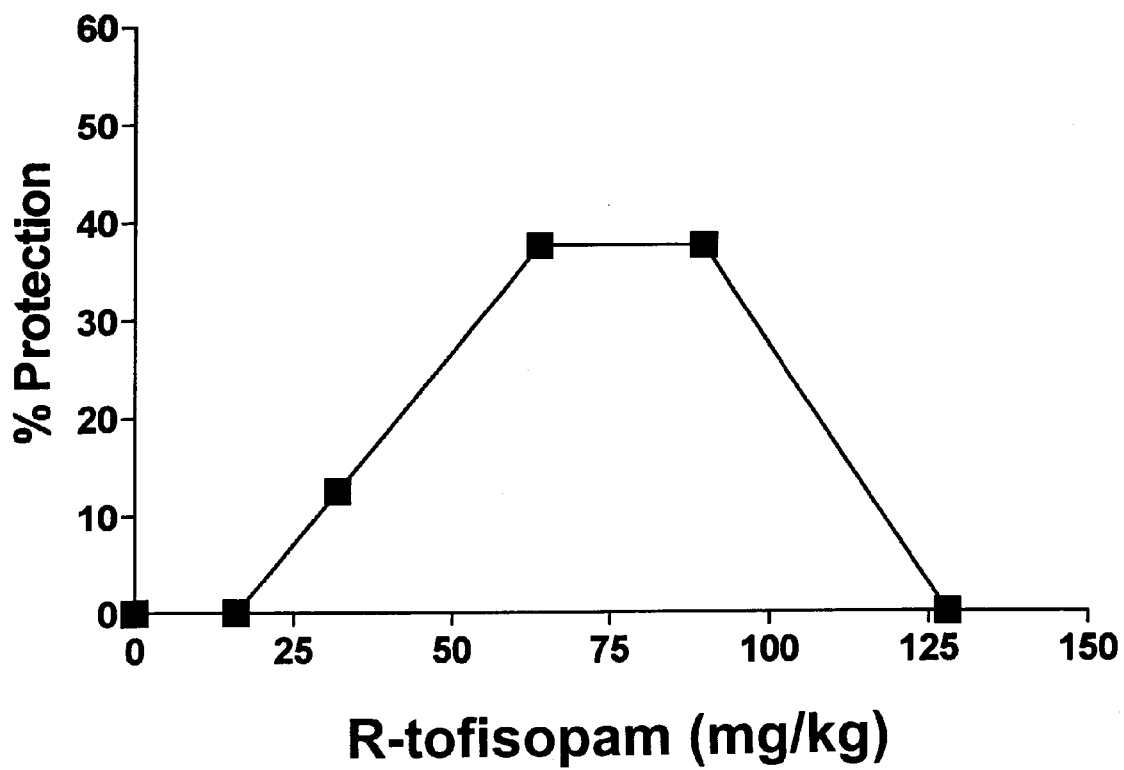
FIG. 5 graphically depicts the anti-convulsant effect of R-tofisopam on picrotoxin-induced seizures in male NSA mice.

The effect of R-tofisopam on picrotoxin-induced seizures in mice is shown in FIG. 5. Although R-tofisopam exhibits anticonvulsant activity at doses of 32 mg/kg and 64 mg/kg, no further increase in protection was observed at 90 mg/kg. In addition, at a dose of 128 mg/kg of R-tofisopam, no protection against picrotoxin-induced seizures in mice was observed. The $ED_{50}$ value could not be calculated because none of the doses produced at least 50% protection from picrotoxin-induced seizures, and also because of the inverted U-shape of the dose response curve (FIG. 5).

Figure 6:
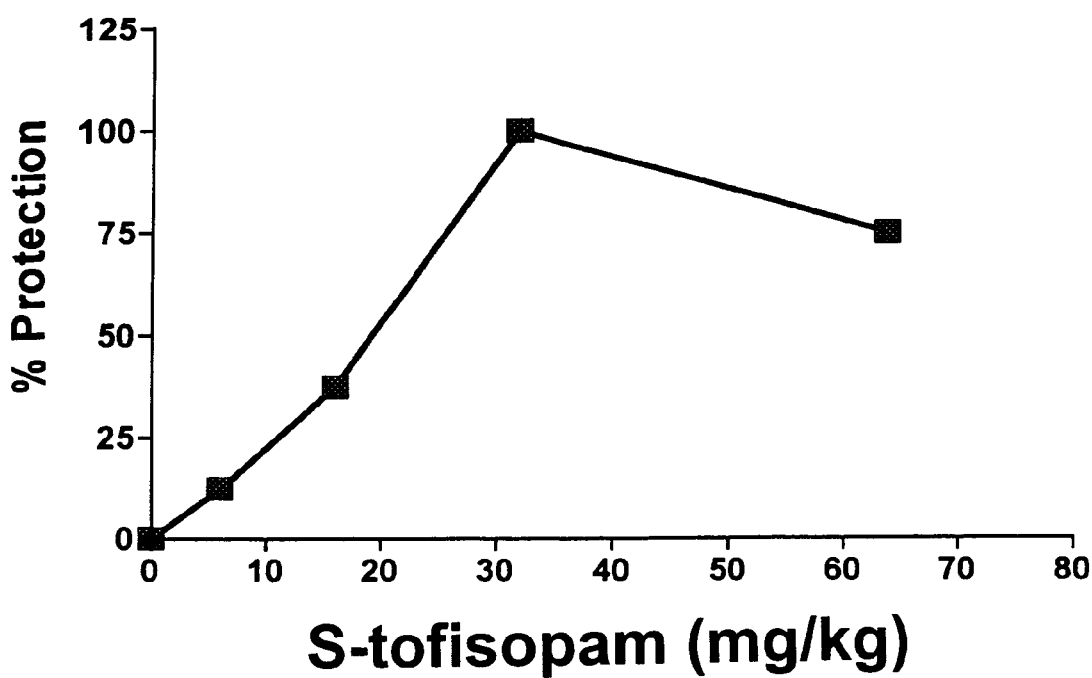
FIG. 6 graphically depicts the dose-dependent anti-convulsant effect of S-tofisopam on picrotoxin-induced seizures in male NSA mice.

S-tofisopam exhibited a dose-dependent anticonvulsant activity with an $ED_{50}$ (95% confidence limits) value of 15.1 (7.6–30.1) mg/kg (see FIG. 6).

TABLE 2

Summary of Anti-convulsant $ED_{50}$ Values for Compounds Tested

| Compound Tested | $ED_{50}$ (95% confidence limit) mg/kg |
| --- | --- |
| diazepam | 0.45 (0.27–0.77) |
| tofisopam | 51.4 (26.8–98.5) |

TABLE 2-continued

Summary of Anti-convulsant $ED_{50}$ Values for Compounds Tested

| Compound Tested | $ED_{50}$ (95% confidence limit) mg/kg |
|---|---|
| R-tofisopam | not calculable |
| S-tofisopam | 15.1 (7.6–30.1) |

These data indicate that both racemic and S-tofisopam have intrinsic anti-convulsant activity, thus, supporting the conclusions from the study described in Example 2. In addition, these results demonstrate that highly pure S-tofisopam displays significantly greater anti-convulsant activity than the racemate compound.

What is claimed is:

1. A composition comprising a therapeutically effective amount of S-tofisopam, a prodrug or a pharmaceutically acceptable salt thereof, substantially free of its (R) enantiomer, with a pharmaceutically acceptable carrier, further comprising another anti-convulsant.

2. The composition according to claim 1, wherein the other anti-convulsant is a benzodiazepine.

3. The composition according to claim 1, wherein the other anti-convulsant is a 1,4-benzodiazepine.

4. The composition according to claim 1, wherein the other anti-convulsant is selected from the group consisting of diazepam, lorazepam, clonazepam, clorazepate and nitrazepam.

5. A composition comprising a therapeutically effective amount of S-tofisopam, a prodrug or a pharmaceutically acceptable salt thereof, substantially free of its (R) enantiomer, with a pharmaceutically acceptable carrier, wherein said composition is a controlled-release pharmaceutical composition.

6. A method of using S-tofisopam as an anti-convulsant agent comprising administering to a subject in need thereof a composition comprising a therapeutically effective amount of S-tofisopam, a prodrug or a pharmaceutically acceptable salt thereof, substantially free of its (R) enantiomer, with a pharmaceutically acceptable carrier.

7. A method of treating convulsions or seizures comprising administering to a subject in need of treatment therefor, a therapeutically effective amount of a composition comprising a therapeutically effective amount of S-tofisopam, a prodrug or a pharmaceutically acceptable salt thereof, substantially free of its (R) enantiomer, with a pharmaceutically acceptable carrier.

8. A method of treating a subject at risk of suffering from a convulsion or seizure comprising administering to said subject a therapeutically effective amount of a composition comprising a therapeutically effective amount of S-tofisopam, a prodrug or a pharmaceutically acceptable salt thereof, substantially free of its (R) enantiomer, with a pharmaceutically acceptable carrier.

9. The method according to claim 7 or 8 wherein the subject is a human.

10. The method according to claim 7 or 8 wherein the amount of S-tofisopam or a prodrug, or a pharmaceutically acceptable salt thereof is 90% or more by weight of the total weight of tofisopam.

11. The method according to claim 7 or 8 wherein the amount of S-tofisopam or a prodrug, or pharmaceutically acceptable salt thereof is 95% or more by weight of the total weight of tofisopam.

12. The method according to claim 7 or 8 wherein the amount of S-tofisopam or a prodrug, or pharmaceutically acceptable salt thereof is 99% or more by weight of the total weight of tofisopam.

13. The method according to claim 7 or 8, wherein the composition is administered intraperitonealy, subcutaneously, intranasally, intramuscularly, intrathecaly, sublingualy, rectaly, by intravenous infusion, transdermal delivery or orally as a tablet, a capsule or a liquid suspension.

14. The method according to claim 7 or 8 wherein said amount is administered in 1 to 4 doses per day.

15. The method according to claim 14 wherein said amount is administered in 1 to 2 doses per day.

16. The method according to claim 7 or 8, wherein the amount of S-tofisopam, prodrug, or a pharmaceutically acceptable salt thereof administered is from approximately 10 mg to 1200 mg.

17. The method according to claim 16 wherein the amount of S-tofisopam, prodrug or pharmaceutically acceptable salt thereof administered is from approximately 50 mg to 600 mg.

18. The method according to claim 16 wherein the amount of S-tofisopam, prodrug or pharmaceutically acceptable salt thereof administered is from approximately 100 mg to 400 mg.

19. The method according to claim 7 or 8, wherein the composition according to claim 1 is administered together or sequentially with another anti-convulsant.

20. The method according to claim 19, wherein the other anti-convulsant is a benzodiazepine.

21. The method according to claim 19, wherein the other anti-convulsant is a 1,4-benzodiazepine.

22. The method according to claim 19, wherein the other anti-convulsant is selected from the group consisting of diazepam, lorazepam, clonazepam, clorazepate and nitrazepam.

* * * * *